United States Patent [19]

Guggenbichler et al.

[11] Patent Number: 5,683,991

[45] Date of Patent: Nov. 4, 1997

[54] BLOCKING THE ATTACHMENT OF GERMS TO HUMAN CELLS

[75] Inventors: Josef Peter Guggenbichler, Fürth; Peter Meissner, Erlangen, both of Germany; Johann Jurenitsch; Andreas De Bettignies-Dutz, both of Vienna, Austria

[73] Assignee: Laevosan-Gesellschaft, Linz, Austria

[21] Appl. No.: 613,991

[22] Filed: Mar. 8, 1996

Related U.S. Application Data

[63] Continuation-in-part of PCT/EP94/03006, Sep. 8, 1994.

[30] Foreign Application Priority Data

Sep. 10, 1993 [DE] Germany ............... 43 30 773.6

[51] Int. Cl.$^6$ .................................................. A61K 31/73
[52] U.S. Cl. ........................ 514/55; 536/114; 536/123.1
[58] Field of Search ............................ 514/53, 54, 55, 514/61, 62; 536/114, 123.1

[56] References Cited

U.S. PATENT DOCUMENTS

| | | | |
|---|---|---|---|
| 2,987,448 | 6/1961 | Goering | 435/272 |
| 4,885,128 | 8/1989 | Lynch et al. | 424/89 |
| 5,055,455 | 10/1991 | Pier | 514/54 |
| 5,180,674 | 1/1993 | Roth | 435/288 |
| 5,192,362 | 3/1993 | Harvey et al. | 106/35 |
| 5,523,014 | 6/1996 | Dolan et al. | 252/122 |

FOREIGN PATENT DOCUMENTS

0 080 442   6/1983   European Pat. Off. .

OTHER PUBLICATIONS

Zopf et al., "Oligosaccharide Anti–Infective Agents," *The Lancet*, 347, 1017–1021 (Apr. 13, 1996).

H–J Gülzow, *Präventive Zahnheilkunde—Grundlagen und Möglichkeiten der Karies und Gingivitisprophylaxe*, Carl Hauser Verlag, München, DE, 1995, only pp. 36–39 and 44–51 and translation into English of the last paragraphs from pp. 48, 51 supplied.

Biologia (Bratislava), 1991, pp. 1081–1087, K. Heinrichova, et al, "Preparation of oligo–(d–galactosiduronic) acids by the action of . . . " with Abstract.

Budavari et al. (eds.), *The Merck Index*, 11th Ed., Merck & Co., Rahway, NY, 1989, see Entry No. 4242 at pp. 678–679 (D–Galacturonic Acid) and Entry No. 6207 (Mucins) at p. 992.

Anderson & King, "Polysaccharides of the Characeae. Part VI. A Non–Esterified Pectic Acid from *Nitella translucens*," *J. Chem. Soc.*, 1961 (Dec.), 5333–5338.

Kohn et al., "Binding of Cadmium and Copper(II) Ions to Oligogalacturonic Acids," *Coll. Czech. Chem. Comm.*, 48(7), 1922–1935 (1983); *Chem. Abstr.*, 99, Abstract No. 189127e (1983); Abstract supplied by applicant.

Springer, "Adhesion Receptors of the Immune System," *Nature*, 346, 425–434 (Aug. 1990).

Berkow et al.(eds.), *Merck Manual of Diagnosis and Therapy*, 16th Ed., Merck Research Laboratories, Rahway, NJ, 1993, only pp. 2480–2481 supplied.

Waldeyer et al., *Anatomie des Menchen für Studierende unde Ärzte Dargestellt Nach Systematischen, Topographischen und Practischen Gesichtspunkten*, Walter de Gruyter, New York, NY, 1986, only pp. 44–47, 196–201 and 204–205 supplied by applicant, in German.

*Primary Examiner*—Gary L. Kunz
*Assistant Examiner*—L. Eric Crane
*Attorney, Agent, or Firm*—Nikaido, Marmelstein, Murray & Oram LLP

[57] ABSTRACT

The invention concerns a pharmaceutical preparation which contains one or several galacturonides as the active substance with a degree of polymerization of ≧2 and a degree of esterification of <20% optionally together with common pharmaceutical carriers, diluents, auxiliary substances and fillers as well as the use of this preparation to block the attachment of germs to mammalian cells.

13 Claims, No Drawings

BLOCKING THE ATTACHMENT OF GERMS TO HUMAN CELLS

CROSS REFERENCE TO RELATED APPLICATION

This application is a continuation-in-part of International Application PCT/EP94/03006, filed Sep. 8, 1994, and designating the U.S.

DESCRIPTION

The present invention concerns a pharmaceutical preparation which contains a galacturonide as the active substance and the use of this preparation to block the attachment of germs to mammalian cells.

Aqueous extracts and juices from various plant products are known in folk medicine and in clinical medicine for their actions against diseases in the intestinal and urogenital tract caused by pathogenic microorganisms. The pharmaceutical action of these preparations in the intestinal tract has previously been attributed to a regulation of the water balance by pectins present in the plant products.

The adherence of germs such as bacterial microorganisms to cells is the first step at the beginning of any infection. It is not until the germs (e.g. bacteria or/and viruses) have attached to specific receptors on cell surfaces and thus avoided the unspecific body defences such as peristalsis, muciliary clearance, secretory flow etc., that they can multiply there, penetrate into the body, develop toxic effects and thus produce a clinical picture.

It would therefore be an elegant step in antimicrobial therapy to block the adherence of germs as an important mechanism of virulence and thus enable the body to wash away germs from cell surfaces or to displace them therefrom. The object of the present invention was therefore to provide a preparation which blocks the attachment of germs to mammalian cells and in particular to epithelial cells.

This object is achieved by a pharmaceutical preparation which is characterized in that it contains one or several galacturonides as the active substance with a degree of polymerization of $\geq 2$ and a degree of esterification of <20%, optionally together with common pharmaceutical carriers, diluents, auxiliary substances and fillers.

The present invention in addition concerns the use of galacturonides with a degree of polymerization of $\geq 2$ for the production of a pharmaceutical preparation for blocking the attachment of germs to mammalian cells.

Surprisingly it was found that the adherence of pathogenic germs such as E. coli to cells, in particular to epithelial cells of the gastrointestinal and urogenital tract, can be substantially reduced (i.e. up to 90%) by carrot soup in the classical preparation according to MORO, diuretic tea (e.g. a mixture of horsetail, yellow cowslip, strawberry leaves and Icelandic moss), coconut milk, cranberries etc. This action is due to the pectins present in the plant products which are essentially chains of 1,4-α-glycosidically linked galacturonides, 20 to 80% of the acidic groups of which are esterified with methanol and which, in addition to galacturonic acid, may contain other sugar building blocks such as glucose, galactose, xylose and arabinose.

Surprisingly it was found that pectins and galacturonides which have previously been used to form jellies, as thickeners or as roughage, can block the attachment of germs to mammalian cells and in particular to human cells.

A galacturonide that is effective in blocking the adherence of germs must have a certain degree of polymerization and preferably have a certain degree of esterification. The term "degree of polymerization" within the sense of the present invention denotes the number of galacturonic acid units which a galacturonide contains. The term "degree of esterification" denotes the percentage of esterified galacturonic acid units (mostly by methyl) of a galacturonide relative to the total number of galacturonic acid units. It was found that a degree of polymerization of $\geq 2$ is necessary to block the adherence of germs to mammalian cells i.e. monomeric galacturonic acid—like numerous other saccharides (e.g. neutral saccharides, glucuronic acid, arabinogalactan, galactose-1-phosphate, glucose-1-phosphate)—does not block the adherence of germs.

In a preferred embodiment of the pharmaceutical preparation according to the invention the degree of esterification of the galacturonides is <20%, especially preferably <10% and even more preferably <5%. Most preferably there are essentially no (<2%) ester groups present.

Galacturonides with a degree of esterification of <20% are obtainable from naturally occurring pectins by complete or partial demethylation e.g. by saponification with alkali.

The degree of polymerization of galacturonides in a pharmaceutical preparation according to the invention is $\geq 2$, i.e. the galacturonide has at least 2 galacturonic acid units. The degree of polymerization of the galacturonide is preferably 2 to 7, even more preferably 2 to 4, particularly preferably 2 to 3 and most preferably 2. I.e. digalacturonide, trigalacturonide, tetragalacturonide, pentagalacturonide, hexagalacturonide, heptagalacturonide and mixtures of several of these substances are preferred galacturonides for the preparations according to the invention, digalacturonide and digalacturonic acid being most preferred. However, depending on the type of application, preparations can also be used which do not contain the best substance with regard to efficacy if this substance is less suitable for a special form of application for technical pharmaceutical reasons.

Galacturonides with a degree of polymerization of 2 to 4 can be obtained from naturally occurring higher molecular pectins by enzymatic hydrolysis using pectin-cleaving enzymes (e.g. pectinases) which are usually obtained on a technical scale from fungi such as Aspergillus or Penicillium species. On the other hand the higher molecular pectins can also be hydrolysed by acid hydrolysis e.g. with HCl.

The pharmaceutical preparation according to the invention can block the attachment of germs in particular of bacterial germs (e.g. E. coli, Streptococci, Haemophilus influenzae, Pneumococci etc.) to mammalian cells or displace germs that have already bound. The pharmaceutical preparations according to the invention are especially suitable for treating infections of the gastrointestinal tract (e.g. abnormal colonization of upper sections of the small intestine in the case of diarrhoeas), of the blood system (haemolytic uraemic syndrome, caused by E. coli 0157), the respiratory passages (e.g. ascending infections in an artificially respirated intensive care patient), the urogenital tract (e.g. recurrent infections of the urinary tract) or/and of the nasopharyngeal space (e.g. by Streptococci, H. influenzae, Pneumococci).

The pharmaceutical preparations according to the invention can on the one hand be administered for an illness which already exists and on the other hand also prophylactically. For example the following modes of administration come into consideration:

a) oral administration such as for the treatment of the gastrointestinal tract, urinary tract, as an additive to rehydration solutions, as a prophylactic agent against abnormal colonization in the gastro-intestinal tract etc. or for intensive care patients with artificial respiration, b) topical applications for example to treat the nasopharyngeal space, urogenital tract etc. and c) parenteral application.

For oral administration, the dosage will generally be in the range of 5 mg–100 mg/kg body weight. On the other hand, for local administration the galacturonide will generally be in a solution in an amount of 0.5–10% by weight.

Galacturonides occur as partial structures of polysaccharides in a large number of foodstuffs and food additives and are thus taken perorally i.e. they are not toxic and are excellently suited for pharmaceutical applications.

The galacturonides used for the pharmaceutical preparations according to the invention can be isolated from polysaccharides found in plants e.g. from carrots, citrus fruits, apples, quinces, sugar beet, coconut milk and other plants or plant products.

In order to isolate the galacturonides the starting materials are preferably comminuted and extracted with hot water. The extracts can be firstly lyophilized or directly processed further. The further processing is preferably carried out using chromatographic methods which enable the galacturonides to be separated from other components of the extract (e.g. other saccharides). Preferred chromatographic separation methods are gel chromatography (e.g. BioGel®, Sephacryl® separation agent) or/and anion exchange chromatography (e.g. DEAE-Sephacel® separation agent). In addition the pectins obtained can be partially or completely saponified to reduce the degree of esterification or/and treated with acid or enzymatically hydrolyzed to reduce the degree of polymerization.

It is intended to further elucidate the invention by the following examples.

EXAMPLE 1

Fresh carrots are washed, peeled and gated. The water-soluble polysaccharides are isolated by extraction with boiling water and subsequent lyophilization.

This is followed by a first gel chromatographic separation step over a column containing BioGel P2 using distilled water as the eluant. The substances which elute with the exclusion volume of this column (SF A) are pooled and separated for a second time by gel chromatography. Sephacryl S-3000 HR serves as the separation material and distilled water is used again as the eluant. Of the two substance peaks which now appear, the one which elutes later is selected.

The third preparation step is an ion exchange chromatography over DEAE-Sephacel with a buffer gradient as the eluant (0.011M to 1M phosphate buffer, pH 6.4). The fraction which is eluted with the higher molarity (SF II) is pooled and processed further. Subsequently a hydrolysis is carried out with HCl (pH 1.00, 37° C., 45 min) and the saccharides are recovered by alcohol precipitation.

The hydrolysate is separated into three groups of substances by gel chromatography (Sephacryl S-2000HR; eluant: distilled water) in which the carbohydrates with the lowest molecular weight (SF 2/3) are collected.

The antiadhesive activity of those fractions that are processed further exceeds that of the by-products which are formed in each case.

The inhibitory activity of the individual substances increased during the processing from 50% in a 0.7% solution (for SF A) to 86.4% in a 0.005% solution (for SF II) to complete inhibition also in a 0.005% solution (for SF 2/3).

This indicates that the concentration required to achieve a certain action becomes considerably lower with increasing purity. This is in contrast to commercially available pectins which have to be used in very high concentrations to achieve similar effects.

EXAMPLE 2

Saponification 11.3 g citrus pectin Grindstedt Company (substance $A_0$) is dissolved in 1200 ml distilled water, admixed with 480 ml 0.5 NaOH and saponified for 15 min at room temperature. The solution is adjusted to pH 4.0 with formic acid. The saponified pectin is precipitated with twice the volume of methanol, dissolved in 200 ml water and the precipitation is repeated in the same manner for a further two times. The precipitate obtained last is dried at 50° C. (substance $A_1$). Weight: 7.15 g Enzymatic hydrolysis The dried precipitate is dissolved with 100 ml 0.1M sodium bicarbonate solution, adjusted to pH 4.5 with formic acid (1M), admixed with 21 mg pectinase 5S from *Aspergillus niger* (Serva Co.) and incubated for 60 min at 60° C. The mixture is heated briefly to 80° C. to activate the enzyme, cooled and precipitated with methanol in the described manner. The precipitate is isolated by centrifugation (20 minutes, 4000 rpm/min) and dried. Weight: 5 g (substance $A_2$).

Thin layer chromatography is used to monitor whether the hydrolysis has produced sufficient amounts of the desired oligogalacturonides.

Thin layer chromatography conditions

Stationary phase: TLC finished plates silica gel 60 (Merck Co.) 10 cm×20 cm

Mobile solvent: ethanol: aqueous acetic acid 25 mM 1:1

Development: at 35° C.

Spray reagent: 200 mg naphthalene-1,3-diol in 50 ml methanol plus 50 ml $H_2SO_4$ (20% g/g)

Chromatography:

1.5 g of the hydrolysis product is dissolved in 15 ml distilled water and subjected to chromatographic fractionation.

| Column: | Glass column from the BioRad Co. (2.5/40 cm) bed volume 150 ml |
|---|---|
| Eluant: | Na formate buffer pH 4.7, gradient in 182 ml steps 0.2, 0.3, 0.4, 0.5, 0.6, 0.7 M |
| Stationary phase: | BioRad AGMP 1 anion exchange resin (equilibrated with eluant) |
| Flow rate: | 3 ml/min |
| Fraction volume: | 22 ml |

The composition of the individual fractions is examined by means of TLC (conditions see above). Fractions of the same composition are pooled and precipitated with twice the volume of acetone. The oligogalacturonides obtained in this manner are isolated by centrifugation (4000 rpm/min) and taken up in 20 ml distilled water. BioRad AG 50 W X-8 cation exchanger (H+) is stirred into the solution in order to convert the galacturonides into the free acid form. After removing the resin and lyophilizing the filtrate a flocculent white powder is obtained.

The results of the inhibition are shown in the following Table 1.

TABLE 1

| Substance name | Characterization | Conc. in % | blockage in 4 |
|---|---|---|---|
| $A_0$ | pectin USP[1] | 0.7 | 15.3 |
| $A_1$ | saponified pectin | 0.2 | 10.0 |
| $A_2$ | partially hydrolysed $A_1$ | 0.05 | 30.2 |
| $F_1$ | neutral di- and trisaccharide | 0.005 | 0.0 |
| $F_2$ | neutral trisaccharide | 0.005 | 0.0 |
| $F_3$ | neutral tetrasaccharide | 0.005 | 0.0 |
| $F_4$ | trigalacturonide | 0.005 | 84.6 |
| $F_5$ | tetragalacturonide containing traces of trigalacturonide | 0.005 | 58.6 |
| $F_6$ | tetragalacturonide | 0.005 | 52.7 |
| $F_7$ | penta-hexagalacturonide | 0.005 | 23.9 |

[1] Citrus pectin (Grindstedt Co.)

Methods for testing the inhibitory efficacy
Adhesion tests

1) Haemagglutination of human O+ erythrocytes: After erythrocytes are brought into contact with germs an agglutination of erythrocytes occurs within 20 seconds in the case of strongly haemagglutinating strains which corresponds to the magnitude of a blood group incompatibility.

Concentration of erythrocytes: 1–1.5%

Germ suspension: turbid suspension OD 1 at 462 nm=$10^9$ germs/ml

In the assessment of the agglutination inhibition, the germs are incubated for 2 h with the carbohydrate solution at the respective desired concentration before adding them to the erythrocytes and then the haemagglutination is evaluated semiquantitatively by eye.

2) Adherence to human uroepithelia: Uroepithelia from morning urine are isolated by centrifugation. Germ suspensions (as above) are brought into contact with the epithelial cells and incubated, subsequently filtered through 8μ polycarbonate filters and washed several times. The filters are removed, placed in physiological NaCl solution and the epithelial cells are shaken off. The NaCl suspension is now centrifuged again and the sediment is mounted on a slide, stained according to May Grünwald and Giemsa and the germs adhering to 50 epithelial cells are counted (blank value).

Controls: epithelial cells without germ contact.

Adherence inhibition: Same method, only the germs are placed for 1 to 3 hours in a solution (0.5, 0.1, 0.05, 0.001%) of the various carbohydrates before addition to the epithelial cell suspension.

Germs used: 4 E. coli wild-type strains which were isolated from patients and 2 commercial strains are used in the same way.

Results

In the microbiological investigations neutral saccharides which exhibited no inhibitory action on adherence at all (e.g. fructans such a inulin, disaccharides such as lactose and lactulose etc.) were also used in addition to the acidic oligosaccharides and polysaccharides listed taxonomically.

Native pectins, i.e. isolated by extraction, have an inhibitory effect on adherence which, however, can be increased by further treatment e.g. saponification and hydrolysis.

Thus in the test mixture described above the pectin isolated by aqueous extraction from carrots in a 1% solution exhibits a 46% inhibition in the test mixture and the purified products exhibit an 80% inhibition in the same mixture at a concentration of 0.1%.

Further results of the microbiological examinations are summarized in the following table 2:

Inhibition of the bacterial adhesion to epithelial cells by selected substances in %:

TABLE 2

| Substance name | Concentration in % | Inhibition in % |
|---|---|---|
| carrot water extract[1] | 1 | 46.0 |
| SF A (see example [1]) | 0.7 | 50.0 |
| SF II (see example [1]) | 0.005 | 86.4 |
| SF 2/3 (see example [1]) | 0.005 | 113.5 |
| polygalacturonic acid from oranges | 0.2 | 99.0 |
| polygalacturonic acid from oranges | 0.05 | 72.0 |
| monogalacturonic acid | 1 | no inhibition |
| digalacturonic acid | 0.005 | 91.7 |
| trigalacturonide[2] | 0.005 | 84.6 |
| tetragalacturonide[2] | 0.005 | 52.7 |
| penta-hexagalacturonide | 0.005 | 23.9 |
| arabinogalactan | 0.005 | no inhibition |
| apple pectin | 0.05 | 20.5 |
| pectinic acid from apples | 0.0.5 | 64.8 |
| galactose-1-phosphate | 0.005 | 3.4 |
| glucose-i-phosphate | 0.005 | no inhibition |
| glucuronic acid | 0.005 | no inhibition |

[1] analogously to example 1
[2] isolated analogously to example 2

As shown in table 2 it can be deduced that there is an increase in efficacy depending on the degree of esterification and the molecular size (the degree of polymerization).

Favourable results are obtained at a degree of polymerization of 2–7.

An improvement of the inhibition is also found by a saponification (i.e. removal of ester groups).

We claim:

1. A method of blocking germs from attachment to epithelial cells, or displacing germs bound to epithelial cells, in a mammalian patient, the method comprising administering to the patient an effective amount of at least one galacturonide having a degree of polymerization of $\geq 2$ and a degree of esterification of <20%.

2. The method of claim 1, wherein the germs are bacterial germs.

3. The method of claim 1, wherein the germs have caused an infection in the patient's gastrointestinal tract, blood system, respiratory passages, urogenital tract and/or the nasopharyngeal space.

4. The method of claim 3, wherein the degree of polymerization is 2 to 4.

5. Method as claimed in claim 1, wherein the degree of esterification of the galacturonide is <10%.

6. Method as claimed in claim 1, wherein the degree of esterification of the galacturonide is <5%.

7. Method as claimed in claim 1, wherein the degree of polymerization of the galacturonide is 2 to 7.

8. Method as claimed in claim 1, wherein the degree of polymerization of the galacturonide is 2 to 6.

9. Method as claimed in claim 1, wherein the degree of polymerization of the galacturonide is 2 to 5.

10. Method as claimed in claim 1, wherein the degree of polymerization of the galacturonide is 2 to 4.

11. Method as claimed in claim 1, wherein the degree of polymerization of the galacturonide is 2 to 3.

12. Method as claimed in claim 1, wherein the degree of polymerization of the galacturonide is 2.

13. Process for blocking the attachment of germs to mammalian epithelial cells, wherein the epithelial cells are contacted by at least one galacturonide having a degree of polymerization of $\geq 2$ and a degree of esterification of <20%.

* * * * *